United States Patent [19]

Mulzer et al.

[11] Patent Number: 5,298,628
[45] Date of Patent: Mar. 29, 1994

[54] PROCESS FOR THE PRODUCTION OF OPTICALLY ACTIVE 4-ARYL-2-PYRROLIDINONES

[75] Inventors: Johann H. Mulzer; Ralf H. Zuhse, both of Berlin, Fed. Rep. of Germany

[73] Assignee: Schering Aktiengesellschaft, Berlin und Bergkamen, Fed. Rep. of Germany

[21] Appl. No.: 877,181

[22] PCT Filed: Sep. 27, 1991

[86] PCT No.: PCT/DE91/00773

§ 371 Date: Jul. 1, 1992

§ 102(e) Date: Jul. 1, 1992

[87] PCT Pub. No.: WO92/06077

PCT Pub. Date: Apr. 16, 1992

[30] Foreign Application Priority Data

Oct. 5, 1990 [DE] Fed. Rep. of Germany ....... 4032055

[51] Int. Cl.$^5$ .................. C07D 207/26; C07D 263/26
[52] U.S. Cl. .................................. 548/551; 548/230; 548/554
[58] Field of Search ............................... 548/551, 230

[56] References Cited

U.S. PATENT DOCUMENTS

| | | |
|---|---|---|
| 4,012,495 | 3/1977 | Schmiechen et al. ............. 424/274 |
| 4,153,713 | 5/1979 | Huth et al. ......................... 424/274 |
| 4,193,926 | 3/1980 | Schmiechen et al. .......... 260/326.55 |

FOREIGN PATENT DOCUMENTS 2413935 10/1975 Fed. Rep. of Germany .
2541855 3/1977 Fed. Rep. of Germany .

OTHER PUBLICATIONS

Marivet et al., "Inhibition of Cyclic Adenosine-3',-5'-Monophosphate Phosphodiesterase from Vascular Smooth Muscle by Rolipram Analogues," J. Med. Chem. 32:1450–1457 (1989).

*Primary Examiner*—David B. Springer
*Attorney, Agent, or Firm*—Millen, White, Zelano, & Branigan

[57] ABSTRACT

Stereoselective process for the production of (4R)- or (4S)-4-aryl-2-pyrrolidinones as well as intermediate products and the stereoselective process for the production of the optically active intermediate compounds.

20 Claims, No Drawings

PROCESS FOR THE PRODUCTION OF OPTICALLY ACTIVE 4-ARYL-2-PYRROLIDINONES

SUMMARY OF THE INVENTION

The invention relates to the process for the production of optically active 4-aryl-2-pyrrolidinones as well as the process for the production of the optically active initial compounds, which are suitable as intermediate products for the production of 4S or 4R enantiomers of 4-aryl-2-pyrrolidinones.

It is known from U.S. Pat. No. 4,012,495 and from WO 86/02268, that 4-aryl-2-pyrrolidinones are compounds with good effectiveness, which are suitable for the treatment of neuroleptic and mental disorders and can also be used for topical treatment of inflammations.

From among the 4-aryl-2-pyrrolidinones, the 4-(3-cyclopentyloxy-4-methoxyphenyl)-2-pyrrolidinone was thoroughly pharmacologically studied. By means of a very costly process and a process that cannot be duplicated on an industrial scale, this compound was converted into its optical antipode and it was noted that both enantiomers represent pharmacologically effective compounds.

Since it is desirable that in chiral active ingredients of pharmaceutical agents only one antipode each is used for the production of pharmaceutical preparations, the object was to develop an industrially applicable process for the production of optically active 4-aryl-2-pyrrolidinones.

According to the process of the invention the desired (4S)-or (4R)-4-aryl-2-pyrrolidinones can be produced in a simple synthesis from the easily accessible optically active initial compounds and can be isolated in high optical purity and good yield without costly separative operations. The recovery of the auxiliary material is to be considered as an additional advantage of the process according to the invention.

The invention relates to a process for the production of (4S)- or (4R)-4-aryl-2-pyrrolidinones of formula I

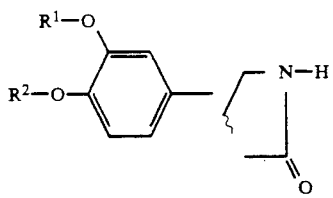

in which $R^1$ is a hydrogen or a hydrocarbon radical with up to 7 carbon atoms optionally interrupted with an oxygen atom and $R^2$ is a $C_{1-4}$ alkyl characterized in that an optically active compound of formula II

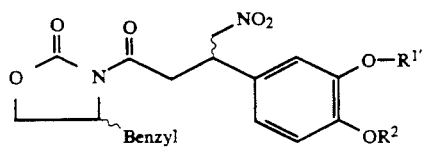

in which $R^{1'}$ has the meaning of R1 or represents an easily cleavable group and $R^2$ is a $C_{1-4}$ alkyl is catalytically reduced with hydrogen, and cyclized and the easily cleavable group is optionally cleaved off and the thus obtained hydroxy group is etherified.

As hydrocarbon radical $R^1$, saturated or unsaturated, straight-chain or branched alkyl groups with 1-6 carbon atoms, preferably 1-4 carbon atoms, are suitable, also $C_{4-6}$-cycloalkylalkyl and cycloalkyl groups with 3-7 carbon atoms and the benzyl group as well as cycloalkyl groups interrupted by an oxygen atom.

As saturated alkyl groups, for example, methyl, ethyl, propyl, isopropyl, butyl, isobutyl, sec. butyl, tert. butyl, pentyl, 2,2-dimethylpropyl and hexyl each are suitable.

As alkenyl and alkynyl groups there can preferably be mentioned: 2-propenyl, 2-propinyl. If hydrocarbon radical $R^1$ means a cycloalkyl group, then cyclopropyl, cyclobutyl, cyclopentyl, cyclohexyl and cycloheptyl are meant, preferably $C_{3-5}$-cycloalkyl groups. Cyclopropylmethyl, cyclopropylethyl and cyclopentylmethyl are to be considered as preferred for the cycloalkylalkyl group.

If the hydrogen carbon radical is interrupted by an oxygen atom, then the cycloalkyl radical, in which a $CH_2$ group is replaced by an oxygen atom is especially meant, and as cyclic ether radical, for example, 3-tetrahydrofuranyl and 3-tetrahydropyranyl can be mentioned.

If the molecule contains a cyclic ether radical, thus another asymmetric center can be present that can be converted to the antipodes in the usual way.

The phrase "easily cleavable group" within the scope of this invention means that the hydroxy protective group is easily cleavable in the usual way either under the reaction conditions or subsequently. As protective groups, for example, the methoxymethyl, methoxyethoxymethyl and also the benzyl group can be mentioned.

As catalysts for the reaction according to the invention the hydrogenation catalysts usually used are suitable such as, for example, Raney nickel or noble metal catalysts such as platinum oxide and palladium/carbon. The reaction takes place at room temperature or with heating to 50° C. at hydrogen standard pressure or elevated hydrogen pressure (about 50 bars) in an aqueous suspension or in inert solvents such as alcohols, ethers or ketones or their mixtures. Generally the reaction is complete after 1 to 10 hours.

If easily cleavable groups, possibly present, are to be cleaved off in the course of the reaction according to the invention, hydrogenation is performed suitably for some time, optionally under pressure or said groups are cleaved off with acid in the usual way.

The etherification of the hydroxy compound can be performed according to the processes described in U.S. Pat. No. 4,012,495. For example, the etherification takes place by reaction with a suitable tosylate, mesylate or halide in the presence of a base with alkali hydroxides and alkali carbonates and tetrabutyl ammonium hydrogen sulfate in inert solvents, such as dimethyl sulfoxide, dimethyl formamide, acetonitrile, tetrahydrofuran, methylene chloride or alcohols at room temperature to the boiling point of the solvent.

The invention further relates to the compounds of formula II, which are optically active initial compounds, from which the compounds of formula I are obtained in one reaction step with very high optical purity.

The invention also relates tot he process for the production of the compounds of formula II, characterized in that an optically active compound of formula III

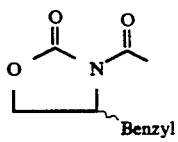

III and a compound of formula IV

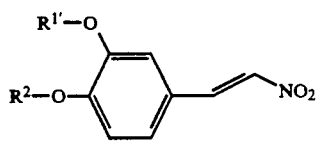

IV in which $R^{1'}$ and $R^2$ have the above meaning, are added.

The addition takes place in the way of a Michael addition, by forming the enolate anion of compound III with strong bases and adding it to the olefin.

The reaction takes place at low temperatures ($-110°$ C. to $-40°$ C.) in aprotic solvents such as cyclic ethers, for example, dioxane or tetrahydrofuran. As bases, for example, alkali salts such as sodium, potassium or lithium salts of hexamethyldisilazane, diisopropylamine or tetramethylpiperidine or hydrides and alcoholates of the mentioned alkali metals are suitable.

Depending on the position of the benzyl group on the oxazolidinone of formula III, after the addition of the olefin, the antipode is obtained in high yields and high optical purity after recrystallization.

Suitably all reactions described here are performed under a protective gas atmosphere, for example, under nitrogen or argon.

The compounds of formulas III and IV used in the process according to the invention as starting material are known compounds or analogues of known compounds, which can be produced stereoselectively according to known methods.

The initial compound of formula III can be produced after acetylation of (4S)- or (4R)-4-benzyl-2-oxazolidinone according to usual methods. The acetylation can be performed, for example, in the presence of strong bases such as butyllithium, lithium diisopropylamide, NaH i.a., in aprotic solvents such as cyclic ethers or hydrocarbons or in the two-phase system according to methods described by V. Illi Synthesis 1979, 387.

The initial compounds of formula IV can be synthesized, e.g. by aldol condensation of the aldehyde with nitromethane (C. B. Gairand, G. R. Lappin J. Org. Chem. 18. 1 (1953))

The following examples are to explain the process according to the invention.

Production of the Initial Compounds 1) 2-(3-Benzyloxy-4-methoxy-phenyl)-1-nitro-(E)-ethane 10 g (41.3 mmol) of 3-benzyloxy-4-methoxy-benzaldehyde, 3.2 g (41.5 mmol, 1 eq) of ammonium acetate and 12 ml of nitromethane are dissolved in 50 ml of glacial acetic acid and refluxed for 12 hours. After cooling, the mixture is concentrated by evaporation in a vacuum, mixed with a little water and shaken out several times with ethyl acetate. After drying on sodium sulfate, the solvent is removed in a water jet vacuum. The solid residue can be recrystallized in ethyl acetate/hexane. The yield is 8.56 g (73%) of golden yellow platelet shaped crystals with a melting point of 126° C.

2) (4S)-3-Acetyl-4-(benzyl)-2-oxazolidinone 10 g (56.4 mmol) of (4S)-4-benzyl-2-oxazolidinone is dissolved under argon atmosphere in 100 ml of abs. THF and is mixed dropwise at $-78°$ C. with 37 ml (59.3 mmol, 1.6M in hexane, 1.05 eq) of n-butyllithium. After 10 min., 4.1 ml (4.5 g, 57.5 mmol, 1.02 eq) of acetyl chloride is instilled. The solution is stirred for 15 more min. under cooling and then 3 hours at room temperature. For working up it is mixed with 50 ml of saturated ammonium chloride solution, the organic solvents are distilled off in a vacuum and the remaining residue is extracted several times with ethyl acetate. After drying on sodium sulfate and concentration by evaporation in a vacuum, the remaining solid is recrystallized in ethyl acetate/hexane. 10.3 g (83%) of colorless needles with melting point of 106° C. is formed.

EXAMPLE 1 a) (4S,3'R) and (4S, 3'S)-3-(3'-(3-Benzyloxy-4methoxyphenyl)-4'-nitrobutanoic acid)-4-benzyl-2-oxazolidinone 3 g (16.9 mmol, 1 eq.) of (4S)-3-acetyl-4-benzyl-2-oxazolidinone dissolved in 10 ml of abs. THF is within 10 minutes in a suspension of 3.1 g (16.9 mmol) of sodium hexamethyldisilazane in 150 ml of abs. THF under argon atmosphere at $-78°$ C. The batch is stirred for 30 minutes and then mixed with a solution of 4.8 g (16.8 mmol, 1 eq) of olefin and 50 ml of abs. THF within one hour. The reaction mixture is stirred another 6 hours with cooling and then heated slowly to room temperature. The reaction is stopped with addition of 50 ml saturated ammonium chloride solution, the organic solvent is removed in a vacuum, the aqueous phase is shaken out with ethyl acetate and the resulting organic fractions are dried on sodium sulfate. The crude product freed from the solvent contains, according to analytic HPLC, (0.6% isopropanol/hexane, flow 2 ml/min. 5 μ Nucleosil 50, 4*250, UV-detection (254 nm) both diastereomers (4S, 3'S) (RT.: 8.45 min) and (4S, 3'R) (RT.: 11.61 min.) in a ratio of 6:94 (de=88%). By a single recrystallization from ethyl acetate/hexane 5.5 g (65%) of a colorless, fine crystalline substance with a melting point of 153° C. is obtained, which according to analytic HPLC has a diastereomeric ratio of (4S, 3'S):(4S, 3'R)=0.5:99.5 (de=99%).

(4S, 3'R) - oxazolidinone derivative $[\alpha]_D^{20} = +28.05$ (c=2.3, chloroform)

(4S, 3'S) - oxazolidinone derivative $[\alpha]_D^{20} = +43.8$ (c=1, chloroform) melting point: 132° C.

b) (4S)-4-(3-Benzyloxy-4-methoxy-phenyl)-2-pyrrolidinone

A suspension of 2 g (3.96 mmol) of (4S, 3'R)-oxazolidinone obtained according to a) and 2 ml of Raney nickel (suspension in water) is shaken out under a hydrogen pressure of 2 bars for 6 hours at room temperature. Then the catalyst is filtered off, the solvent is drawn off and the crude product is subjected to a column chromatographic purification (methylene chloride/acetone, 7:3).

Isolated are:

440 mg of (4S)*4-(-3-benzyloxy-4 methoy phenyl)-2-pyrrolidinone
[α]$_D^{20}$ = +28.65 (c = 0.5, chloroform) melting point: 121° C.
320 mg of (4S)-4-(-3-hydroxy-4-methoxy-phenyl)-2-pyrrolidinone
[α]$_D^{20}$ = +36.7 (c = 1.8, chloroform) melting point 145° C.
470 mg of (4S)-4-benzyl-2-oxazolidinone, melting point 86° C.

I claim:

1. A process for production of an optically active 4-aryl-2-pyrrolidinone of formula I

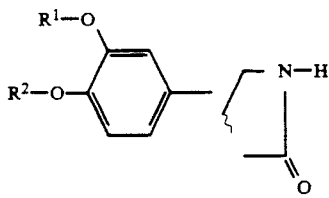     I wherein
R$^1$ is hydrogen or a hydrocarbon radical with up to 7 carbon atoms and optionally interrupted with an oxygen atom; and
R$^2$ is C$_{1-4}$-alkyl, said process comprising: catalystically reducing with hydrogen and cyclizing, in the presence of a hydrogenation catalyst, an optically active compound of formula II

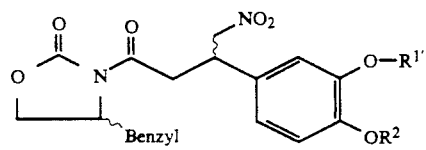     II wherein
R$^{1'}$ has the meaning of R$^1$ or is a cleavable hydroxy protective group, and
R$^2$ is C$_{1-4}$-alkyl, and
optionally cleaving off said cleavable hydroxy protective group and etherifying the resultant hydroxy group, to obtain a compound of formula I.

2. An optically active compound of formula II

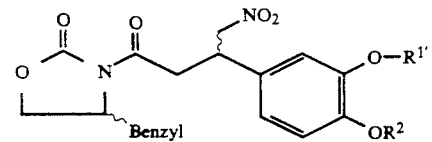     II wherein
R$^{1'}$ is hydrogen, a hydrocarbon radical having up to 7 carbon atoms and optionally interrupted with an oxygen atom, or a cleavable hydroxy protective group, and
R$^2$ is C$_{1-4}$-alkyl.

3. A process for production of a compound of formula II

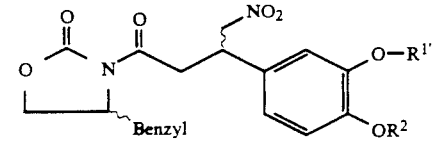     II wherein
R$^{1'}$ is hydrogen, a hydrocarbon radical having up to 7 carbon atoms and optionally interrupted with an oxygen atom, or a cleavable hydroxy protective group, and
R$^2$ is C$_{1-4}$-alkyl,
comprising performing a Michael addition, in the presence of a base, between an optically active compound of formula III

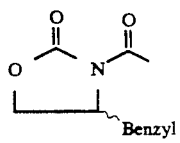     III and a compound of formula IV

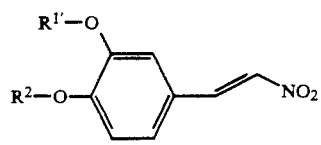     IV wherein R$^{1'}$ and R$^2$ have the meanings indicated above.

4. A process according to claim 1, wherein R$^1$ is a saturated or unsaturated, straight-chain or branched alkyl group having 1-6 carbon atoms, a C$_{4-6}$-cycloalkylalkyl, a C$_{3-7}$-cycloalkyl, a C$_{3-7}$-cycloalkyl which is interrupted by an oxygen atom, or benzyl.

5. A process according to claim 4, wherein R$^1$ is a saturated or unsaturated, straight-chain or branched alkyl group having 1-6 carbon atoms.

6. A process according to claim 5, wherein R$^1$ is a saturated or unsaturated, straight-chain or branched alkyl group with 1-4 carbon atoms.

7. A process according to claim 4, wherein R$^1$ is methyl, ethyl, propyl, isopropyl, butyl, isobutyl, sec-butyl, tert.-butyl, pentyl, 2,2-dimethylpropyl, hexyl, 2-propenyl, 2-propinyl, cyclopropyl, cyclobutyl, cyclopentyl, cyclohexyl, cycloheptyl, cyclopropylmethyl, cyclopropylethyl, cyclopentylmenthyl, 3-tetrahydrofuranyl or 3-tetrahydropyranyl.

8. A process according to claim 1, wherein catalytic reduction with hydrogen and cyclization is performed in the presence of Raney nickel, platinum oxide or palladium/carbon.

9. A process according to claim 4, wherein catalytic reduction with hydrogen and cyclization is performed in the presence of Raney nickel, platinum oxide or palladium/carbon.

10. A process according to claim 1, wherein catalytic reduction with hydrogen and cyclization is conducted in an aqueous suspension.

11. A process according to claim 1, wherein catalytic reduction with hydrogen and cyclization is conducted in an inert solvent.

12. A process according to claim 1, wherein R$^{1'}$ is a cleavable hydroxy protective group which is cleaved off during catalytic reduction with hydrogen and cyclization.

13. A process according to claim 1, wherein R$^{1'}$ is a cleavable hydroxy protective group and, after catalytic reduction with hydrogen and cyclization, R$^{1'}$ is cleaved off and the resultant hydroxy group is etherified.

14. A process according to claim 12, wherein $R^1$ is methoxymethyl, methoxyethoxymethyl or benzyl.

15. A process according to claim 13, wherein $R^1$ is methoxymethyl, methoxyethoxymethyl or benzyl.

16. A process according to claim 12, wherein etherification is conducted in the presence of a base in an inert solvent.

17. A process according to claim 1, wherein $R^{1'}$ is $R^1$.

18. A process according to claim 4, wherein $R^{1'}$ is $R^1$.

19. A process according to claim 3, wherein said Michael addition is conducted at a temperature of $-110°$ — $-40°$ C. in an aprotic solvent.

20. A process for production of an optically active 4-aryl-2-pyrrolidinone of formula I

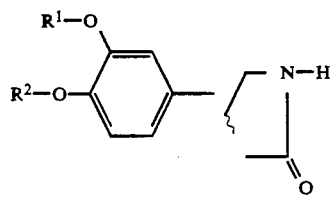

wherein
$R^1$ is hydrogen or a hydrocarbon radical with up to 7 carbon atoms and optionally interrupted with an oxygen atom; and
$R^2$ is $C_{1-4}$-alkyl,
said process comprising:
performing a Michael addition, in the presence of a base, between an optically active compound of formula III

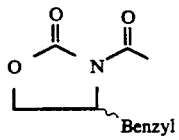

and a compound of formula IV

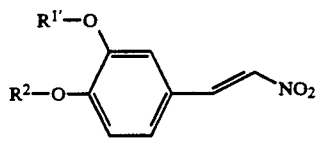

wherein
$R^{1'}$ is hydrogen, a hydrocarbon radical having up to 7 carbon atoms and optionally interrupted with an oxygen atom, or is a cleavable hydroxy protective group, and
$R^2$ is $C_{1-4}$-alkyl,
to obtain diastereomers of formula II

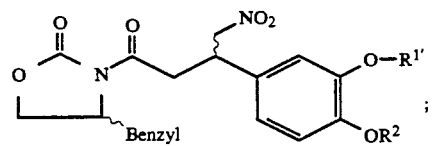

catalytically reducing with hydrogen and cyclizing, in the presence of a hydrogenation catalyst, an optically active compound of formula II; and
optionally cleaving off said cleavable hydroxy protective group and etherifying the resultant hydroxy group to obtain a compound of formula I.

* * * * *